United States Patent
Stumber et al.

(10) Patent No.: US 9,556,476 B2
(45) Date of Patent: Jan. 31, 2017

(54) METHOD FOR ACTIVE HYBRIDIZATION IN MICROARRAYS WITH DENATURING FUNCTION

(75) Inventors: Michael Stumber, Korntal-Muenchingen (DE); Martina Daub, Weissach (DE); Jochen Rupp, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 1062 days.

(21) Appl. No.: 13/808,110

(22) PCT Filed: Jun. 1, 2011

(86) PCT No.: PCT/EP2011/059053
§ 371 (c)(1),
(2), (4) Date: Apr. 15, 2013

(87) PCT Pub. No.: WO2012/004062
PCT Pub. Date: Jan. 12, 2012

(65) Prior Publication Data
US 2013/0210660 A1    Aug. 15, 2013

(30) Foreign Application Priority Data
Jul. 6, 2010    (DE) .................. 10 2010 030 962

(51) Int. Cl.
C40B 30/04    (2006.01)
C12Q 1/68    (2006.01)
B01L 3/00    (2006.01)
B01L 7/00    (2006.01)

(52) U.S. Cl.
CPC ........... *C12Q 1/6837* (2013.01); *B01L 3/5027* (2013.01); *B01L 7/52* (2013.01); *B01L 2200/10* (2013.01); *B01L 2300/0636* (2013.01); *B01L 2300/0816* (2013.01); *B01L 2400/0481* (2013.01); *B01L 2400/0487* (2013.01); *C40B 30/04* (2013.01)

(58) Field of Classification Search
None
See application file for complete search history.

(56) References Cited

U.S. PATENT DOCUMENTS

| | | |
|---|---|---|
| 5,508,197 A | 4/1996 | Hansen et al. |
| 5,587,128 A | 12/1996 | Wilding et al. |
| 6,168,948 B1 | 1/2001 | Anderson et al. |
| 6,660,517 B1 | 12/2003 | Wilding et al. |
| 7,713,692 B2 | 5/2010 | Kawaguchi |

(Continued)

FOREIGN PATENT DOCUMENTS

| | | | |
|---|---|---|---|
| DE | 10 2008 002 336 A1 | 12/2009 | |
| EP | 1 652 912 A1 | 5/2006 | |

(Continued)

OTHER PUBLICATIONS

International Search Report corresponding to PCT Application No. PCT/EP2011/059053, mailed Dec. 7, 2011 (German and English language document) (7 pages).

*Primary Examiner* — Christian Boesen
(74) *Attorney, Agent, or Firm* — Maginot, Moore & Beck LLP

(57) ABSTRACT

A method for active hybridization in microarrays includes pumping an already prepared sample through a denaturing unit with a microarray and then through a reaction region which is spatially separate from the denaturing unit. The denatured reactive sample components are hybridized in the reaction region.

14 Claims, 1 Drawing Sheet

(56) References Cited

U.S. PATENT DOCUMENTS

2004/0009525 A1 1/2004 Kawaguchi
2004/0141856 A1 7/2004 Scurati
2007/0254372 A1 11/2007 Bickel et al.

FOREIGN PATENT DOCUMENTS

| | | |
|---|---|---|
| JP | 2003-315337 A | 11/2003 |
| JP | 2004-194652 A | 7/2004 |
| JP | 2008-253227 A | 10/2008 |
| JP | 2009-34052 A | 2/2009 |
| WO | 2007/122819 A1 | 11/2007 |

METHOD FOR ACTIVE HYBRIDIZATION IN MICROARRAYS WITH DENATURING FUNCTION

This application is a 35 U.S.C. §371 National Stage Application of PCT/EP2011/059053, filed on Jun. 1, 2011, which claims the benefit of priority to Serial No. DE 10 2010 030 962.1, filed on Jul. 6, 2010 in Germany, the disclosures of which are incorporated herein by reference in their entirety.

BACKGROUND

The present disclosure relates to a method for active hybridization with a separate denaturation function.

Microarrays are known as modern molecular-biology test systems. They allow the parallel analysis of several thousand single detections in a small amount of biological sample material. Consequently, various forms of microarrays have been established, which are classified according to the nature of their interactions. These include, firstly, nucleic acid-based microarrays, which are used, for example, to detect DNA, mRNA or rRNA of particular genes of organisms. For this purpose, cDNA, oligonucleotides or fragments of PCR products which are complementary to the mRNA are printed on support materials ("spotted microarrays"). In the case of the "oligonucleotide microarrays", synthetically produced oligonucleotides are applied to, for example, glass supports. The oligonucleotides acting as probes generate, on the supports, the greatest possible density of information on a very small space in a manner similar to a computer chip, and so microarrays are also readily referred to as "gene chips" or "biochips".

Further known embodiments are protein arrays, which detect, for example, antigen-antibody, enzyme-substrate, receptor-protein or other protein-protein interactions. It is also possible to detect and quantify binding of nucleic acids to proteins.

When using microarrays in microbiology, the biomolecules from a sample which is, in general, processed and pretreated are applied to the microarray, and, on the individual sites ("spots") of the microarray, specific binding reactions occur, which consequently provide information about the presence of particular molecules, for example DNA fragments, in the sample. A prerequisite for this binding reaction is the presence of the DNA or RNA as single strands, and so a prior denaturation step is imperative. In the case of generally increasing automation, there is a multiplicity of approaches for performing very many individual steps of the analysis within one device unit in order to thus save time and costs. This includes the use of micropumps, by means of which the extremely small sample volumes are transported within the device units; see in this regard, for example, US 2004/0141856A1.

The actual binding procedure or the hybridization to the probes of the microarray can in turn occupy two or more hours, since the movement of the particles is in accordance with Brownian motion and therefore takes place very slowly. Also, as a result, only some of the target molecules present in the sample reach the respective capture structure, i.e., the probes.

SUMMARY

It is an object of the disclosure to provide a method which comprises the denaturation of the biomolecules, for example the melting of the nucleic acids present as double strands into single strands, and the binding of the denatured biomolecules to the probes of the microarray, and speeds up the actual hybridization, without adversely affecting the sensitivity of the analysis.

The present disclosure therefore provides a method for active hybridization to at least one probe of a microarray, comprising the following steps:

a) providing a sample liquid containing reactive constituents, b) introducing the sample liquid into a pump route comprising at least one pump unit, at least one temperature-controlled denaturation unit and at least one temperature-controlled reaction area which is spatially separated from the denaturation unit and has at least one microarray, c) pumping the sample liquid, d) denaturing the reactive constituents of the sample liquid in the denaturation unit and e) hybridizing the denatured constituents to at least one probe of the microarray in the reaction area.

Hybridization to a microarray generally takes place by means of diffusional movement of the biomolecules in the sample liquid. Said diffusional movement can be supported by shaking or vibrating the sample liquid. For this purpose, various systems, for example the Maui® Mixer from Bio-Micro Systems Inc., are known. The method according to the disclosure, in contrast, provides the crucial advantage that the diffusion process is supported by pump movements of the sample liquid. The pumping can generate a uniform, controlled flow of the sample liquid, which ensures that a continually sufficient number of binding particles is maintained above the probes. Depletion of binding particles, as continually takes place in diffusion-controlled processes, is therefore counteracted. The sample liquid can directly flow onto the reaction area containing the microarray, or else the reaction area containing the microarray can be arranged inside a reaction chamber. However, in any case, a uniform, controlled flow over the probe(s) of the microarray has to be ensured. Moreover, the reaction area can be loaded with two or more microarrays, on which one or more probes are arranged in each case.

In one of the embodiments, the pump route is arranged as a circuit, and this additionally supports the uniform, controlled flow of the sample liquid over the probes of the microarray. The pump speed is set such that the sample flows in the reaction area at a few mm/min. This supports the otherwise diffusion-limited hybridization reaction. For example, the hybridization reaction proceeds at about 54° C. in the case of nucleic acids.

Further positive effects arise as a result of the denaturation unit being spatially separated from the reaction area, and so denaturation of the single strands can be initially performed. In the case of nucleic acids, the sample liquid is guided across an area of higher temperature (e.g., 94° C.) to melt the double strands into single strands. The presence of the nucleic acids present in the sample as single strands is a prerequisite for the following binding to the probes of the microarray (hybridization) in the reaction area arranged downstream. The speed and the sensitivity of the binding reactions on the spots of the microarray are improved as a result of the increase in available single-stranded molecules. This is especially the case when the pump route is circularly constructed, and nucleic acids which are once again or still present as double-stranded molecules are fed cyclically to repeat denaturation and subsequent hybridization. Therefore, the still unbound molecules can bind to the probes of the microarray in a following round.

In any case, the present method shifts the binding equilibrium of the biomolecules and increases the sensitivity of the analysis, and so even the detection of few biomolecules in a sample volume is possible.

The spatial separation of the denaturation unit from the reaction area makes the setting of optimized conditions for the particular reactions possible. Here, in particular, the setting of an optimal temperature for the particular biomolecules is of crucial importance. For example, temperature ranges of at least 90° C., preferably from 94 to 98° C., are selected for the denaturation of nucleic acids. For the hybridization reaction of nucleic acids, the temperature is held at, for example, 54° C. in the reaction area. In any case, the separate temperature control in the denaturation unit and the reaction area is important.

In a further embodiment, there is a cooling step between the denaturation of the biomolecules in the denaturation unit and the hybridization in the reaction area, and so it can be ensured that the denatured biomolecules enter the reaction area at an optimal temperature. The cooling can be effected using an appropriately designed cooling route.

Various methods are useful for temperature control of the denaturation unit and/or hybridization unit (e.g., resistance heaters, infrared heaters, hot-air blowers and/or Peltier elements). Since the hybridization in the reaction area generally proceeds at lower temperatures, it must be ensured that the sample volume from the pump route is at the desired target temperature when it enters the reaction area. The reaction area therefore has a reliable temperature control and can, if necessary, be temperature-controlled just like the denaturation unit.

Since the hybridization reaction generally proceeds at lower temperatures than the denaturation reaction, cooling of the sample to a particular hybridization temperature is a priority. In a first temperature range, the biomolecules are denatured and split or melted. With a second temperature range which is lower with respect to the first temperature range, hybridization to the probes of the microarray is ensured, and monitored by means of an optimized temperature control.

Besides a structure in the form of a multicomponent system, the method can be realized with particular advantage as a lab-on-a-chip system, which, for example, is formed from particular polymers as support substrate. Here, the pump function can be implemented by various pumps. Suitable for use in the present method are, in particular, micropumps integrated on the chip, for example micromembrane pumps or peristaltic micropumps. Useful as externally operated pumps are, for example, syringe pumps or peristaltic pumps. Pumps of this kind are described in, for example, DE 10 2008 002 336 A1 and part of the prior art.

In a further embodiment, the denaturation unit and the pump unit are formed as a structural unit. Here, the temperature control is effected via a heatable pump.

Alternatively, the denaturation unit is present as a meandering channel which is heatable to the temperature required for denaturation. On such a structure, the mixing of the sample within the circuit is, in particular, advantageous. The associated improved homogeneity of the sample also improves the actual hybridization reaction. The meandering channel preferably has a microstructure, and so this component can be realized in a lab-on-a-chip system too.

In a further embodiment, the reaction area is connected to a second pump route, via which flush liquids and/or reaction liquids required for the hybridization can be fed to the reaction area. In a particular embodiment, the additional pump route has valves to separate the denaturation unit from the hybridization unit. Alternatively, the substances required for the reaction can also be fed to the method via the central pump route. However, in any case, there is at least one appropriate inflow or inlet and an appropriate outlet, via which both the sample liquid and reaction liquids and/or flush liquids can be fed or discharged.

In a further embodiment, the detection of the microarray can directly follow the hybridization step, and so the hybridization and the detection of the microarray can proceed in one unit and, if necessary, are structurally combined. However, a lab-on-a-chip system is particularly advantageous.

BRIEF DESCRIPTION OF THE DRAWINGS

Further advantages and advantageous designs of the method according to the disclosure are illustrated by the figures and elucidated in the following description. It should be noted that the figures only have a descriptive character and are not intended to restrict the disclosure in any way. The figures use the following reference signs:

1: Pump unit
2: Fluid connection
3: Denaturation unit
4: Reaction area
5: Microarray
6: Inlet
7: Outlet
8: Support substrate

FIG. 1 diagram of a device for carrying out the method, comprising a pump route arranged as a circuit and having a denaturation unit in the form of a meandering channel and a reaction area comprising a microarray.

FIG. 2 diagram of a device for carrying out the method, in which the structure is in the form of a lab-on-a-chip system, wherein the pump route arranged as a circuit comprises a pump unit, a denaturation unit and a reaction area.

DETAILED DESCRIPTION

Figure 1:
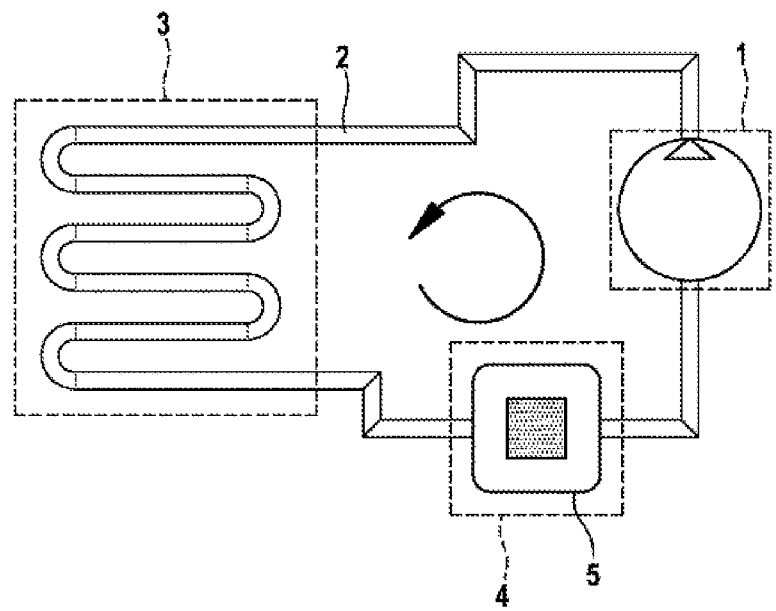
FIGS. 1 and 2 illustrate the method according to the disclosure. In particular, the two figures show.

FIG. 1 shows a possible structure for implementing the method according to the disclosure. The reaction area 4 together with the microarray 5 contained therein is connected via fluid connections 2 to a pump route in which the sample liquid is pumped using a pump unit 1 in a circuit—thus indicated by the arrow, in the middle of the figure, showing the direction of flow. The denaturation unit 3 used is a meandering channel. Here, the sample liquid is heated to a temperature range optimized for the particular biomolecules, and so the denaturation thereof takes place. The actual hybridization reaction on the probes of the microarray 5 in the reaction area 4 subsequently takes place in a second temperature range. In the pump unit 1, the sample liquid can, if necessary, be set to a third temperature range.

Figure 2:
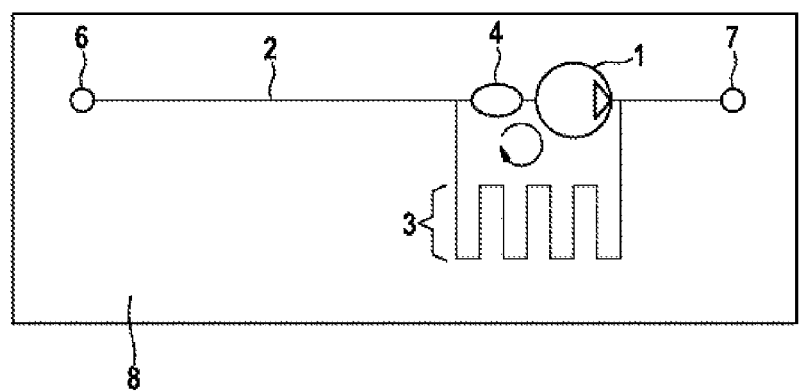

FIG. 2 shows a diagram of a device for carrying out the method according to the disclosure in the form of a lab-on-a-chip system. The system comprises a support substrate 8 on which an inlet 6 and an outlet 7 for the sample liquid and the required reagents and flush liquids are arranged. The sample is introduced via fluid connections 2 into the pump route by means of the pump unit 1. The denaturation unit 3 is in the form of a meandering channel on a microscale. Following the denaturation unit is the reaction area 4 containing the actual microarray 5 for the hybridization of the denatured biomolecules. In a lab-on-a-chip system, the pump unit 1, the denaturation unit 3 and the reaction area 4 are also subject to respective temperature control and/or temperature regulation.

The invention claimed is:

1. A method for active hybridization to at least one probe of a microarray, comprising:
   a. providing a sample liquid containing reactive constituents,
   b. introducing the sample liquid into a pump route comprising at least one pump unit, at least one temperature-controlled denaturation unit and at least one temperature-controlled reaction area which is spatially separated from the at least one temperature-controlled denaturation unit and has at least one microarray,
   c. pumping the sample liquid,
   d. denaturing the reactive constituents of the sample liquid in the at least one temperature-controlled denaturation unit and
   e. hybridizing the denatured constituents to at least one probe of the at least one microarray in the at least one temperature-controlled reaction area.

2. The method as claimed in claim 1, wherein the at least one pump unit and the at least one temperature-controlled denaturation unit form a structural unit.

3. The method as claimed in claim 1, further comprising cooling the sample liquid after denaturing in the at least one temperature-controlled denaturation unit and before hybridizing in the at least one temperature-controlled reaction area.

4. The method as claimed in claim 1, further comprising detecting the microarray after hybridizing the denatured constituents in step e.

5. The method as claimed in claim 1, wherein the at least one pump unit comprises a micromembrane pump.

6. The method as claimed in claim 5, wherein the at least one pump unit is integrated within the pump route.

7. The method as claimed in claim 1, wherein the pump route is arranged as a circuit and a uniform, controlled flow of the sample liquid is generated by pumping the sample liquid in step c.

8. The method as claimed in claim 1, wherein the at least one temperature-controlled denaturation unit comprises a meandering channel.

9. The method as claimed in claim 1, wherein the at least one temperature-controlled denaturation unit comprises at least one unit configured to control temperature.

10. The method as claimed in claim 1, wherein the at least one temperature-controlled reaction area is connected to a second pump route configured to feed at least one of flush liquids and reaction liquids required for hybridizing to the at least one temperature-controlled reaction area.

11. The method as claimed in claim 1, wherein the at least one pump unit comprises a peristaltic micropump.

12. The method as claimed in claim 11, wherein the at least one pump unit is arranged off chip.

13. The method as claimed in claim 5, wherein the at least one pump unit is arranged off chip.

14. The method as claimed in claim 11, wherein the at least one pump unit is integrated within the pump route.

* * * * *